(12) United States Patent
Kirkpatrick et al.

(10) Patent No.: US 6,676,989 B2
(45) Date of Patent: Jan. 13, 2004

(54) METHOD AND SYSTEM FOR IMPROVING THE EFFECTIVENESS OF MEDICAL STENTS BY THE APPLICATION OF GAS CLUSTER ION BEAM TECHNOLOGY

(75) Inventors: Allen R. Kirkpatrick, Lexington, MA (US); Robert K. Becker, Danvers, MA (US); Avrum Freytsis, Salem, MA (US)

(73) Assignee: Epion Corporation, Billerica, MA (US)

( * ) Notice: Subject to any disclaimer, the term of this patent is extended or adjusted under 35 U.S.C. 154(b) by 0 days.

(21) Appl. No.: 09/901,204

(22) Filed: Jul. 9, 2001

(65) Prior Publication Data

US 2002/0051846 A1 May 2, 2002

Related U.S. Application Data

(60) Provisional application No. 60/217,045, filed on Jul. 10, 2002.

(51) Int. Cl.$^7$ .......................... B05D 3/00; C23C 14/28; C23C 14/34; C23C 16/00
(52) U.S. Cl. ...................... 427/2.28; 427/2.24; 427/595; 204/192.34; 204/298.27; 204/298.28; 204/298.36; 118/723 CB
(58) Field of Search ................. 204/192.11, 192.34, 204/298.04, 298.15, 298.23, 298.27, 298.28, 298.36; 118/723 CB, 730, 500, 66; 156/345; 427/224, 228, 595

(56) References Cited

U.S. PATENT DOCUMENTS

| | | | | |
|---|---|---|---|---|
| 5,814,194 A | * | 9/1998 | Deguchi et al. | 204/192.1 |
| 5,980,974 A | * | 11/1999 | Armini et al. | 427/2.27 |
| 6,231,598 B1 | * | 5/2001 | Berry et al. | 623/1.15 |
| 2002/0014407 A1 | * | 2/2002 | Allen et al. | 204/298.36 |
| 2002/0017454 A1 | * | 2/2002 | Kirkpatrick | 204/192.34 |
| 2002/0017455 A1 | * | 2/2002 | Kirkpatrick et al. | 204/192.34 |

* cited by examiner

*Primary Examiner*—Steven H. VerSteeg
(74) *Attorney, Agent, or Firm*—Perkins, Smith & Cohen, LLP; Jerry Cohen

(57) ABSTRACT

Numerous studies suggest that the current popular designs of coronary stents are functionally equivalent and suffer a 16 to 22 percent rate of restenosis. Although the use of coronary stents is growing, the benefits of their use remain controversial in certain clinical situations or indications due to their potential complications. The application of gas cluster ion beam (GCIB) surface modification such as smoothing or cleaning appears to reduce these complications and lead to genuine cost savings and an improvement in patient quality of life. The present invention is directed to the use of GCIB surface modification to overcome prior problems of thrombosis and restenosis. The atomic level surface smoothing of stents utilizing GCIB substantially reduces undesirable surface micro-roughness in medical coronary stents.

33 Claims, 10 Drawing Sheets

METHOD AND SYSTEM FOR IMPROVING THE EFFECTIVENESS OF MEDICAL STENTS BY THE APPLICATION OF GAS CLUSTER ION BEAM TECHNOLOGY

CROSS REFERENCE TO RELATED APPLICATIONS

This application claims priority of U.S. provisional application Ser. No. 60/217,045 entitled "Method and System for Improving the Effectiveness of Medical Stents by the Application of Gas Cluster Ion Beam Technology", filed Jul. 10, 2002, the provisional application being incorporated herein by reference.

FIELD OF THE INVENTION

This invention relates generally to medical devices such as coronary stents and, more particularly to a method and system for smoothing medical coronary stents using gas cluster ion beam technology.

BACKGROUND OF THE INVENTION

A coronary stent is an implantable medical device that is used in combination with balloon angioplasty. Balloon angioplasty is a procedure used to treat coronary atherosclerosis. Balloon angioplasty compresses built-up plaque against the walls of the blocked artery by the inflation of a balloon at the tip of a catheter inserted into the artery during the angioplasty procedure. Unfortunately, the body's response to this procedure often includes thrombosis or blood clotting and the formation of scar tissue or other trauma-induced tissue reactions at the treatment site. Statistics show that restenosis or renarrowing of the artery by scar tissue after balloon angioplasty occurs in up to 35 percent of the treated patients within only six months after these procedures, leading to severe complications in many patients.

To reduce restenosis, cardiologists are now often placing a small, typically expandable, metal tubular device called a coronary stent at the site of blockage during balloon angioplasty. The goal is to have the stent act as a scaffold to keep the coronary artery open after the removal of the balloon. Stents have been shown to reduce the rate of restenosis to from 16 to 22 percent.

The problem is there are also serious complications associated with the use of coronary stents. Coronary restenotic complications associated with stents occur in from 16 to 22 percent of all cases within six months after insertion of the stent and are now believed to be caused, in part, by surface micro-roughness of the stents themselves. Because of the substantial financial costs associated with treating the complications of restenosis, such as catheterization, restenting, intensive care, etc., a reduction in restenosis rates would save money and reduce patient suffering.

It is therefore an object of this invention to provide an atomic level surface smoothing of medical coronary stents.

It is a further object of this invention to provide surface modification of medical coronary stents by gas cluster ion beams to decrease complication of restenosis.

SUMMARY OF THE INVENTION

The objects set forth above as well as further and other objects and advantages of the present invention are achieved by the invention described hereinbelow.

Numerous studies suggest that the current popular designs of coronary stents are functionally equivalent and suffer a 16 to 22 percent rate of restenosis. Although the use of coronary stents is growing, the benefits of their use remain controversial in certain clinical situations or indications due to their potential complications. The application of gas cluster ion beam (GCIB) surface modification such as smoothing or cleaning appears to reduce these complications and lead to genuine cost savings and an improvement in patient quality of life. The present invention is directed to the use of GCIB surface modification to overcome prior problems of thrombosis and restenosis. The atomic level surface smoothing of stents utilizing GCIB in this invention substantially reduces undesirable surface micro-roughness in medical coronary stents.

For a better understanding of the present invention, together with other and further objects thereof, reference is made to the accompanying drawings and detailed description and its scope will be pointed out in the appended claims.

DETAILED DESCRIPTION OF THE PREFERRED METHODS AND EMBODIMENTS

Figure 1:
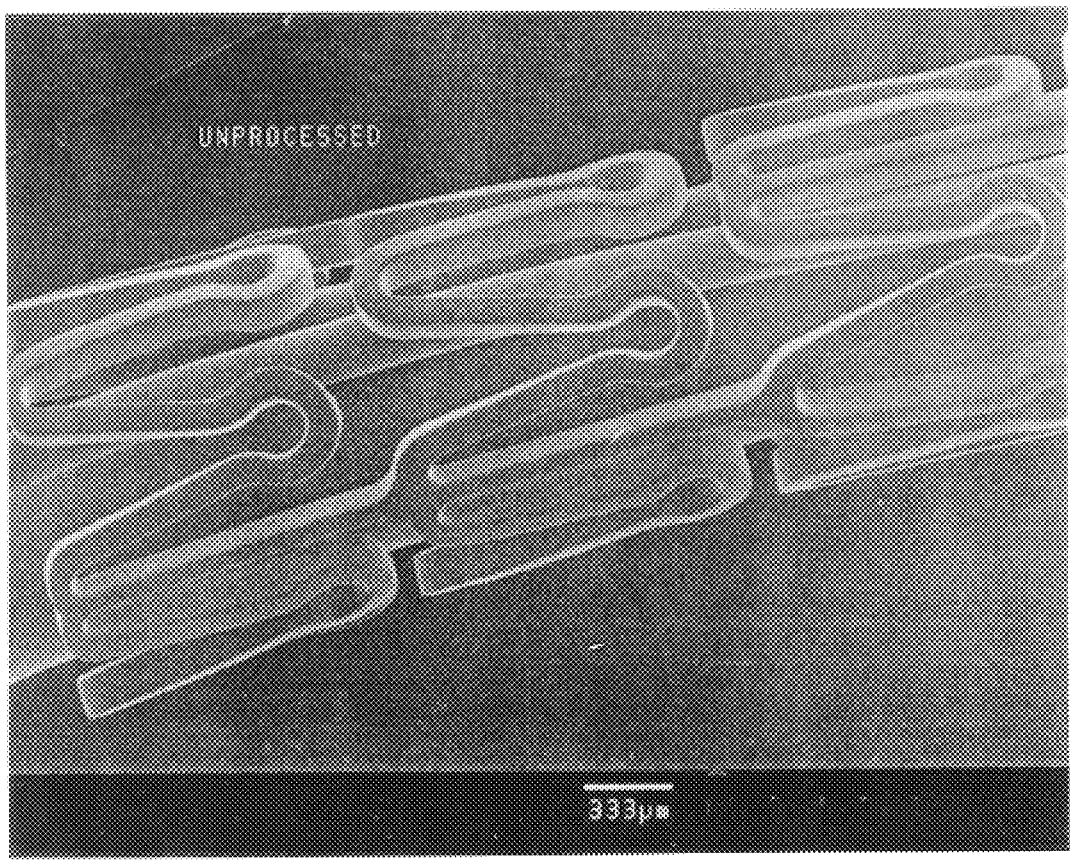
FIG. 1 is a scanning electron micrograph of a portion of a prior art medical coronary stent.

FIG. 1 shows a low magnification scanning electron microscope image of a typical medical coronary stent. Stents are typically fabricated from metal in any of several forms of expandable mesh, with the example in FIG. 1 shown only to illustrate one type and not for limitation. In general, coronary stents may have any of a variety of expanding mesh patterns that have surfaces that may be oriented in a variety of directions. They are typically inserted into an artery while in a unexpanded condition and then expanded in place at the location of the stenosis being treated, where they are intended to remain as a permanent means of assuring a clear lumen in the artery. Note that in FIG. 1, the stent is supported on a wire passing through the stent, but which is not part of the stent.

Figure 2:
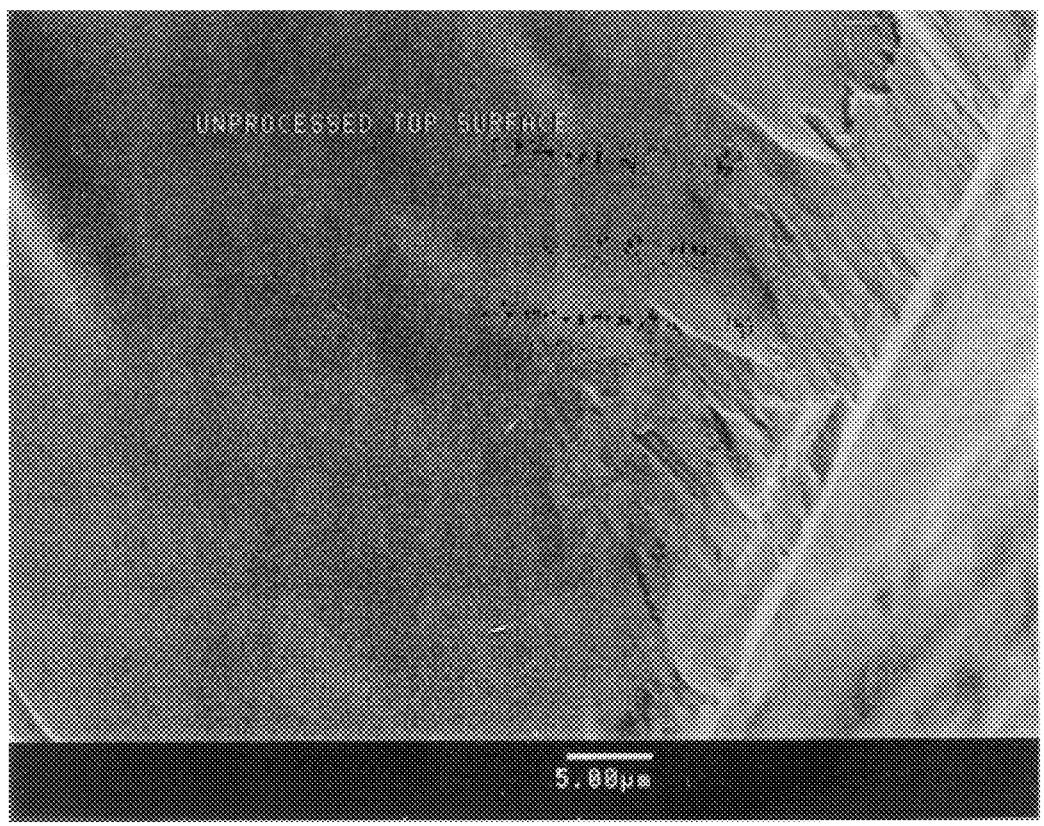
FIG. 2 is a high magnification scanning electron micrograph of a portion of a prior art medical coronary stent showing unsatisfactory surface finish.

FIG. 2 is a high magnification scanning electron microscope image of a portion of an exterior surface of a stent of the type shown in FIG. 1. Considerable surface roughness is present. FIG. 2 shows an exterior surface, but similar micro-roughness is also typically observed on all surfaces of prior art stents. It is believed that such roughness contributes to restenotic complications, and that although the roughness of the exterior surface is perhaps most important, roughness on interior surfaces may also contribute.

Beams of energetic ions, electrically charged atoms or molecules accelerated through high voltages under vacuum, are widely utilized to form semiconductor device junctions, to etch surfaces by sputtering, and to enhance the properties of thin films. Gas cluster ions are formed from large numbers of weakly bound atoms or molecules sharing common electrical charges and accelerated together through high voltages to have high total energies. Cluster ions disintegrate upon impact and the total energy of the cluster is shared among the constituent atoms. Because of this energy sharing, the atoms are individually much less energetic than in the case of conventional ions or ions not clustered together and, as a result, the atoms penetrate to much shorter depths. Surface sputtering effects can be orders of magnitude stronger than corresponding effects produced by conventional ions, thereby making important microscale surface smoothing effects possible that are not possible in any other way.

The concept of gas cluster ion beam (GCIB) processing has only emerged over the past decade. Using a GCIB for dry etching, cleaning, and smoothing of materials is known in the art and has been described, for example, by Deguchi, et al. in U.S. Pat. No. 5,814,194, "Substrate Surface Treatment Method", 1998. Because ionized clusters containing on the order of thousands of gas atoms or molecules may be formed and accelerated to modest energies on the order of a few thousands of electron volts, individual atoms or molecules in the clusters may each only have an average energy on the order of a few electron volts. It is known from the teachings of Yamada in, for example, U.S. Pat. No. 5,459, 326, that such individual atoms are not energetic enough to significantly penetrate a surface to cause the residual subsurface damage typically associated with plasma polishing. Nevertheless, the clusters themselves are sufficiently energetic (some thousands of electron volts) to effectively etch, smooth, or clean hard surfaces.

Because the energies of individual atoms within a gas cluster ion are very small, typically a few eV, the atoms penetrate through only a few atomic layers, at most, of a target surface during impact. This shallow penetration of the impacting atoms means all of the energy carried by the entire cluster ion is consequently dissipated in an extremely small volume in the top surface layer during a period of $10^{-12}$ seconds. This is different from the case of ion implantation which is normally done with conventional ions and where the intent is to penetrate into the material, sometimes penetrating several thousand angstroms, to produce changes in the surface properties of the material. Because of the high total energy of the cluster ion and extremely small interaction volume, the deposited energy density at the impact site is far greater than in the case of bombardment by conventional ions.

Figure 3:
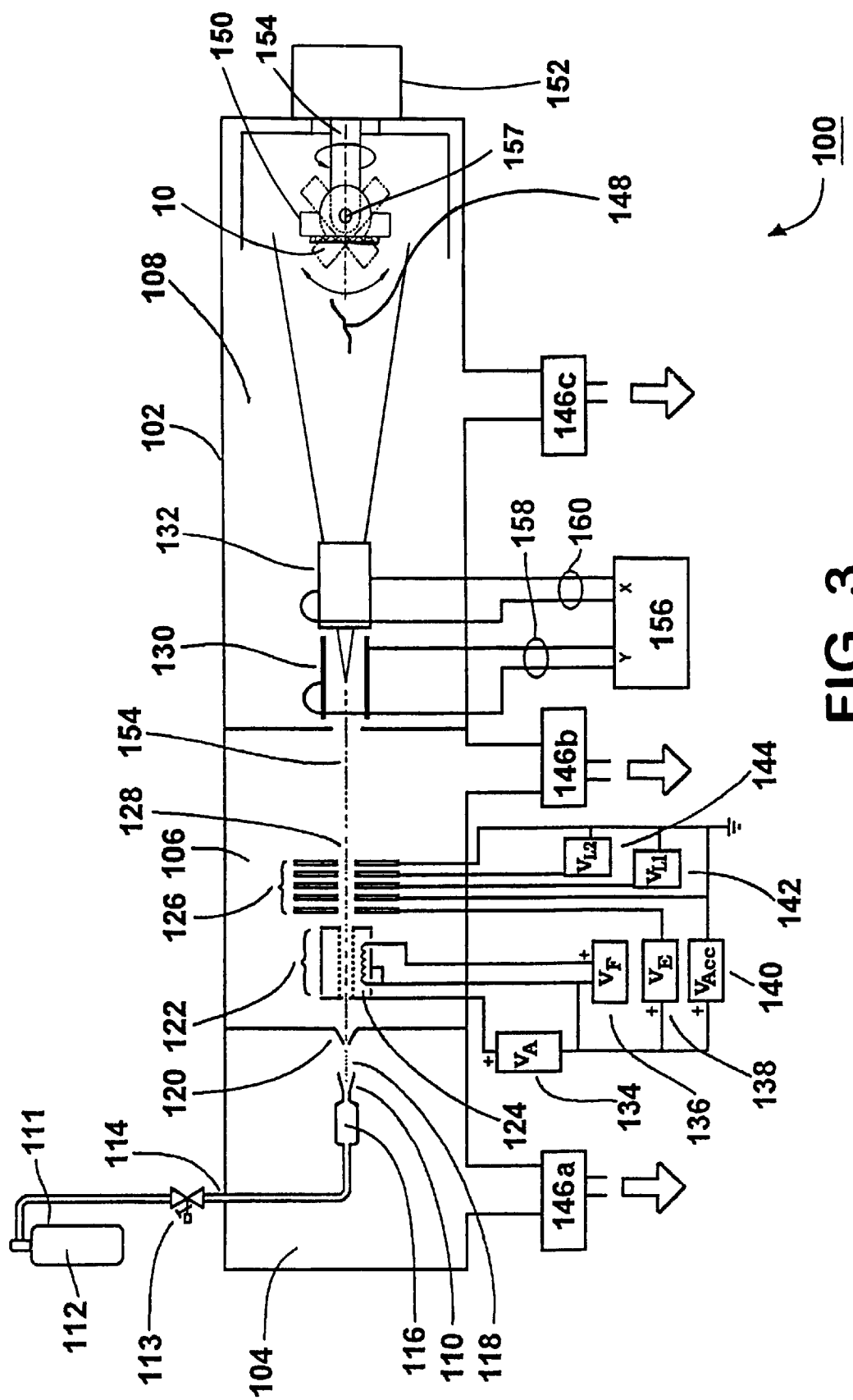
FIG. 3 is a schematic view of a gas cluster ion beam processing system of the present invention.

Reference is now made to FIG. 3 of the drawings which shows an embodiment of the gas cluster ion beam (GCIB) processor 100 of this invention utilized for the surface smoothing of a coronary stent 10. Although not limited to the specific components described herein, the processor 100 is made up of a vacuum vessel 102 which is divided into three communicating chambers, a source chamber 104, an ionization/acceleration chamber 106, and a processing chamber 108 which includes therein a uniquely designed workpiece holder 150 capable of positioning the medical device for uniform smoothing by a gas cluster ion beam.

During the smoothing method of this invention, the three chambers are evacuated to suitable operating pressures by vacuum pumping systems 146a, 146b, and 146c, respectively. A condensable source gas 112 (for example argon, $O_2$, or $N_2$) stored in a cylinder 111 is admitted under pressure through gas metering valve 113 and gas feed tube 114 into stagnation chamber 116 and is ejected into the substantially lower pressure vacuum through a properly shaped nozzle 110, resulting in a supersonic gas jet 118. Cooling, which results from the expansion in the jet, causes a portion of the gas jet 118 to condense into clusters, each consisting of from several to several thousand weakly bound atoms or molecules. A gas skimmer aperture 120 partially separates the gas molecules that have not condensed into a cluster jet from the cluster jet so as to minimize pressure in the downstream regions where such higher pressures would be detrimental (e.g., ionizer 122, high voltage electrodes 126, and process chamber 108). Suitable condensable source gases 112 include, but are not necessarily limited to argon, nitrogen, carbon dioxide, oxygen.

After the supersonic gas jet 118 containing gas clusters has been formed, the clusters are ionized in an ionizer 122. The ionizer 122 is typically an electron impact ionizer that produces thermoelectrons from one or more incandescent filaments 124 and accelerates and directs the electrons causing them to collide with the gas clusters in the gas jet 118, where the jet passes through the ionizer 122. The electron impact ejects electrons from the clusters, causing a portion the clusters to become positively ionized. A set of suitably biased high voltage electrodes 126 extracts the cluster ions from the ionizer 122, forming a beam, then accelerates the cluster ions to a desired energy (typically from 1 keV to several tens of keV) and focuses them to form a GCIB 128 having an initial trajectory 154. Filament power supply 136 provides voltage $V_F$ to heat the ionizer filament 124. Anode power supply 134 provides voltage $V_A$ to accelerate thermoelectrons emitted from filament 124 to cause them to bombard the cluster containing gas jet 118 to produce ions. Extraction power supply 138 provides voltage $V_E$ to bias a high voltage electrode to extract ions from the ionizing region of ionizer 122 and to form a GCIB 128. Accelerator power supply 140 provides voltage $V_{Acc}$ to bias a high voltage electrode with respect to the ionizer 122 so as to result in a total GCIB acceleration energy equal to $V_{Acc}$ electron volts (eV). One or more lens power supplies (142 and 144, for example) may be provided to bias high voltage electrodes with potentials ($V_{L1}$ and $V_{L2}$ for example) to focus the GCIB 128.

A medical coronary stent 10 to be processed by the GCIB processor 100 is held on a workpiece holder 150, disposed in the path of the GCIB 128. In order for the uniform smoothing of the stent 10 to take place, the workpiece holder 150 is designed in a manner set forth below to manipulate the stent 10 in a specific way.

Figure 4:
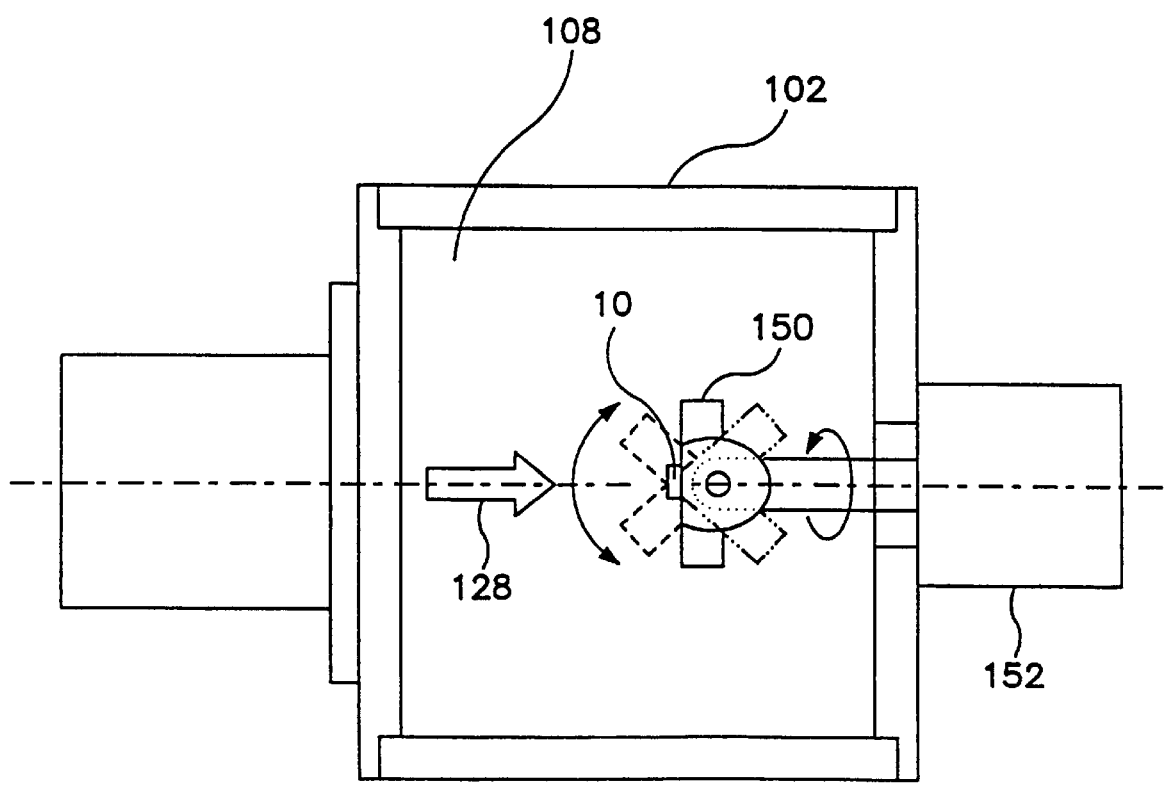
FIG. 4 is an exploded view of a portion of the gas cluster ion beam processing system showing the workpiece holder.

Referring now to FIG. 4 of the drawings, it is known that the most rapid smoothing of metals by GCIB processing results when the incidence of the GCIB on the surface is non-grazing and that almost no smoothing results when the incidence of the GCIB on the surface is grazing. Most rapid smoothing can be achieved when the angle of beam incidence is within +/−45 degrees of normal incidence. Useful smoothing can be achieved with angles of beam incidence within about +/−65 degrees of normal incidence. Since stents have multiply-oriented surfaces that are non-planar, it is necessary that the stents must be oriented to the GCIB in a large range of positions during processing to assure that all exterior and interior surfaces are smoothed. This requires a fixture or workpiece holder 150 with the ability to be fully articulated to orient all non-planar surfaces of stent 10 to be modified within that specific angle tolerance at a constant exposure level for process optimization and uniformity. Since stents typically have a substantially open structure (like that shown in FIG. 1), with suitable manipulation, interior surfaces may be exposed to GCIB processing by manipulating the stent with respect to the GCIB so as to allow beam to flow through openings in the stent mesh and to become incident on the interior surfaces. More specifically, when smoothing a coronary stent 10, the workpiece holder 150 is rotated and articulated by a mechanism 152 located at the end of the GCIB processor 100. The articulation/rotation mechanism 152 preferably permits 360 degrees of device rotation about longitudinal axis 154 and sufficient device articulation about an axis 157 perpendicular to axis 154 to expose all of the stent's surfaces to near-normal (within +/−45 degrees from normal) beam incidence.

Referring again to FIG. 3, under certain conditions, depending upon the size of the coronary stent 10, a scanning system may be desirable to produce uniform smoothness. Although not necessary for GCIB processing, two pairs of orthogonally oriented electrostatic scan plates 130 and 132 may be utilized to produce a raster or other scanning pattern over an extended processing area. When such beam scanning is performed, a scan generator 156 provides X-axis and Y-axis scanning signal voltages to the pairs of scan plates 130 and 132 through lead pairs 158 and 160 respectively. The scanning signal voltages are commonly triangular waves of different frequencies that cause the GCIB 128 to be converted into a scanned GCIB 148, which scans the entire surface of the stent 10.

When beam scanning over an extended region is not desired, processing is generally confined to a region that is defined by the diameter of the beam. The diameter of the beam at the stent's surface can be set by selecting the voltages ($V_{L1}$ and/or $V_{L2}$) of one or more lens power supplies (142 and 144 shown for example) to provide the desired beam diameter at the workpiece.

Figure 5:
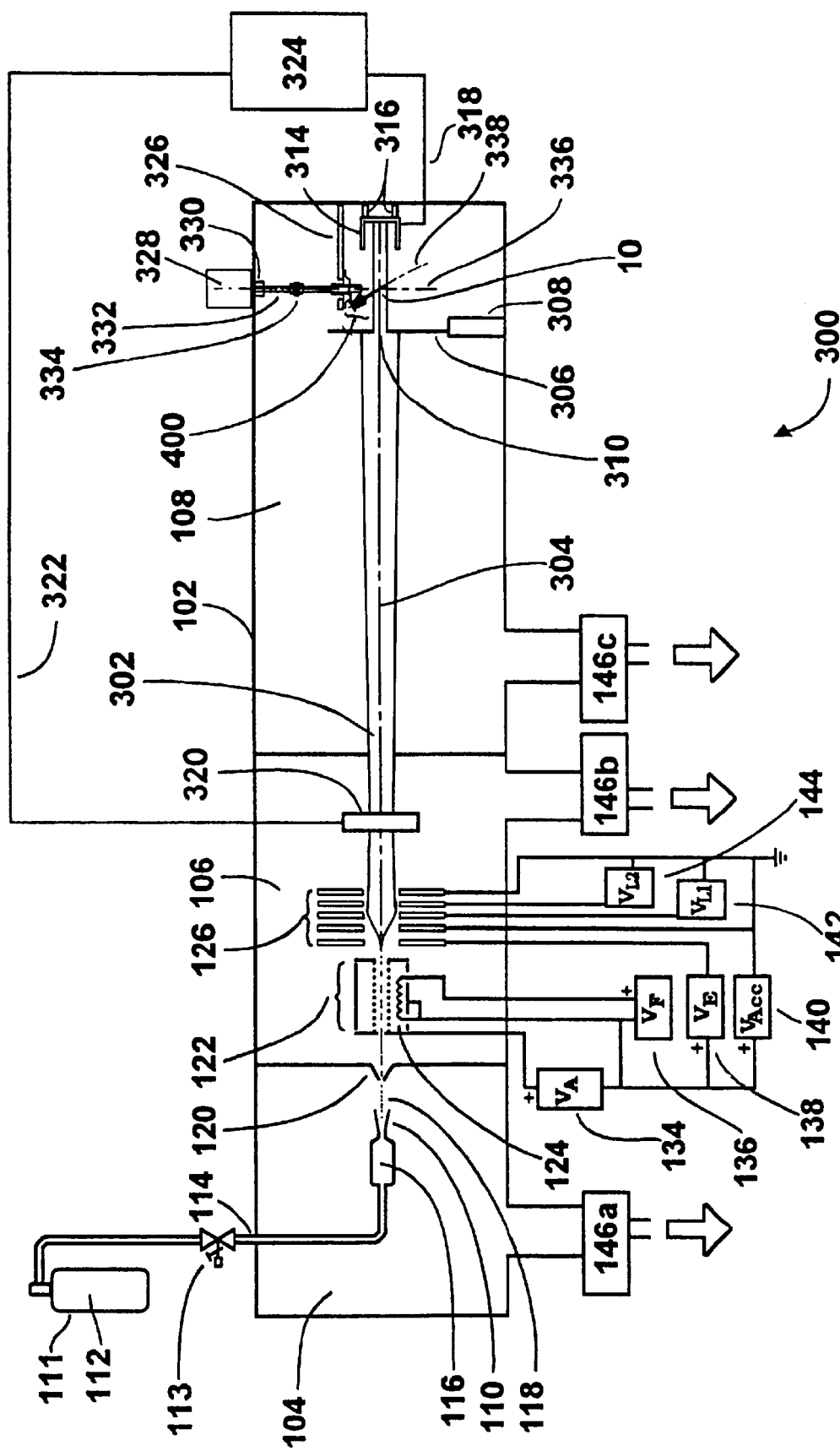
FIG. 5 is a schematic view of an alternate embodiment of a gas cluster ion beam processing system of the present invention.

FIG. 5 of the drawings shows a preferred embodiment gas cluster ion beam (GCIB) processor 300 of this invention utilized for the surface smoothing of a coronary stent 10. In this preferred embodiment, the lens power supplies 142 and 144 provide voltages chosen to form an approximately cylindrical or slightly conical GCIB 302 of substantially uniform beam current density traveling along a beam axis 304 and directed onto a beam aperture plate 306. Beam aperture plate 306 has a beam defining aperture 310, having a predetermined area, A, so that a portion of GCIB 302 passes through the aperture 310 for collection by a current collecting device 314. The area, A, is predetermined to be large (for example, approximately 3 cm$^2$) compared to the effective cross-sectional area of any stent, 10, that may be introduced to the GCIB 302 for processing. The beam aperture plate is held in a fixed position by a beam aperture plate support 308. The current collecting device 314 is preferably a Faraday cup, as shown, or some other form of current collecting electrode(s) and is supported by electrically insulating supports 316. The current collecting device 314 has a current conducting lead 318 for conducting collected current to a conventional dose processor 324. A beam gate 320 is disposed in the path of GCIB 302. Beam gate 320 has an open state and a closed state. When beam gate 320 is open, GCIB 302 passes through beam gate 320 and a portion of GCIB 302 passes through aperture 310 and is collected by current collecting device 314. When beam gate 320 is closed, GCIB 302 is interrupted and does not pass through beam gate 320. An electrical control cable 322 conducts control signals from a conventional dose processor 324 to beam gate 320, the control signals controllably switching beam gate 320 to either of its open or closed states for enabling or disabling the transmission of GCIB 302 therethrough. A workpiece (medical stent) manipulator 400, shown more clearly in FIG. 6 and described in more detail hereinafter, rotatably disposes a medical coronary stent 10 downstream of the beam defining aperture 310 so that the stent 10 is irradiated by the portion of GCIB 302 that passes through the aperture 310. Manipulator 400 is mechanically supported by manipulator support member 326. A rotary motor 328, has a motor shaft 332 that passes through a rotary vacuum feedthrough 330 to transmit rotary motion to the manipulator 400 through motor shaft 332 and flexible shaft coupler 334. The manipulator 400 holds stent 10 and manipulates it so that it rotates about two axes of rotation, axis 336 and axis 338, respectively, and clearly shown in FIG. 6. Both axis 336 and axis 338 substantially instersect the beam axis 304. The dose processor 324 may be one of many conventional dose control circuits that are known in the art and may include as a part of its control systems all or part of a programmable computer system. In operation, the dose processor 324 signals the opening of the beam gate 320 to irradiate the stent 10. The dose processor 324 measures the beam current, $I_b$, collected by the current collecting device 314, due to the portion of the GCIB 302 that passes through the beam defining aperture 310 and uses the value of the predetermined area, A, to compute a mean dose rate, r, in ions/area/sec according to known techniques. The effective cross-sectional area presented to the GCIB 302, downstream of the beam defining aperture, by the stent is very small compared to the predetermined area, A, of the beam defining aperture 310. Therefore, the fraction of the beam current collected by the stent is small enough to be negligible for dosimetry purposes and is ignored. It is realized that if it were necessary for improved dosimetry accuracy, the beam current collected by the stent could be combined with that collected by the current collection device for dosimetry purposes. The dose processor 324 integrates the dose rate, r, with respect to time to compute the accumulated dose, d, received by the stent 10. When the dose, d, received by the stent 10 reaches a predetermined required dose, D, the dose processor 324 closes the beam gate 320 and processing is complete. During processing, workpiece manipulator 400 rotates stent 10 about two axes to assure that all surfaces of the stent are exposed to irradiation by the GCIB.

Figure 6:
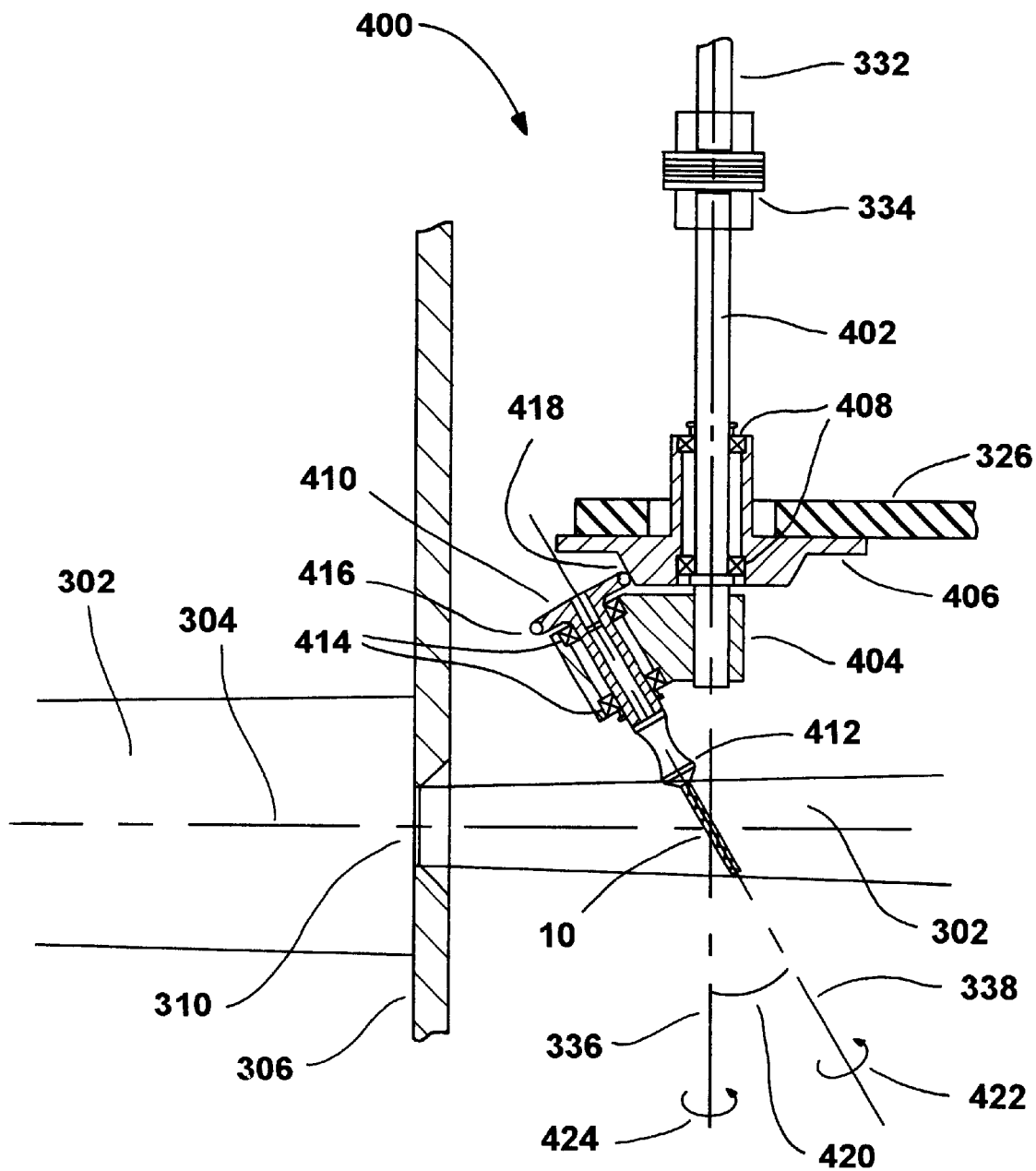
FIG. 6 is a detailed schematic view of the stent manipulator of the alternate embodiment of the invention.

FIG. 6 shows the workpiece manipulator 400 in greater detail. Manipulator 400 is mechanically supported by manipulator support member 326, only partially shown in FIG. 6, but fully shown in FIG. 5. A rotary motor shaft 332, only partially shown in FIG. 6, but fully shown in FIG. 5, transmits rotary motion to the manipulator 400 through shaft coupler 334 and manipulator shaft 402. Manipulator shaft 402 is has a rotary motion 424 about rotary axis 425, and is disposed so as to cause rotary axis 425 to be approximately perpendicular to and to pass through beam axis 304. A manipulator stator 406 is fixedly attached to manipulator support member 326. Manipulator shaft 402 passes through manipulator stator 406 and is rotat~bly supported by a pair of rotary bearings 408. A manipulator rotor 404 is fixedly attached to manipulator shaft 402 and rotates therewith. A wheeled spindle 410, is rotatably supported by a second pair of rotary bearings 414 and passes through manipulator rotor 404. Spindle 410 rotates about axis 338 with a rotary motion 422. Manipulator rotor 404 disposes rotary axis 338 so as to pass through rotary axis 336 approximately at the intersection of rotary axis 336 with the beam axis 304. Manipulator rotor 404 also disposes rotary axis 338 so as to be at a predetermined angle 420, between about 15 degrees and about 45 degrees, with respect to axis 336, preferably approximately 45 degrees. An elastic spindle tread 416, preferably in the form of a Viton® Kalrez® O-ring, frictionally engages both spindle 410 and a (preferably conical) friction surface 418 of manipulator stator 406 so as to drive a rotation of spindle 410 about axis 338, when manipulator rotor 404 rotates about axis 336. Diameters of the spindle tread 410 and conical friction surface 418 are predetermined to be in a ratio N:M, where N/M is not an integer and where M/N is not an integer, but where M/N preferably has a non-integral value that is near the value of a small integer such as 2 (for example 7:15 or 8:15 or) so that rotary motion 422 has a rotational frequency of about (but not precisely) twice the rotational frequency of rotary motion 424. The value of M/N may be a rational or irrational number. By preferably avoiding small integer ratios (for example N:M= 1:2 or 2:1 or 1:3 or 3:1), it is assured that precise repetition of any particular beam incidence on the workpiece cannot be repeated for at least several revolutions of the workpiece, thus assuring great diversity of beam incidence on the workpiece. It is preferred that N is less than M so that the rotation about axis 422 is more rapid than the rotation about axis 425. A workpiece holder 412 is fixedly attached to spindle 410 for holding a workpiece such as a cylindrical medical coronary stent 10. During GCIB processing, the rotational speed of motor 328 is such as to assure at least several revolutions and preferably at least 100 revolutions of the stent 10 abOLIt axis 338 in the GCIB 302 during the processing time.

Figure 7B:
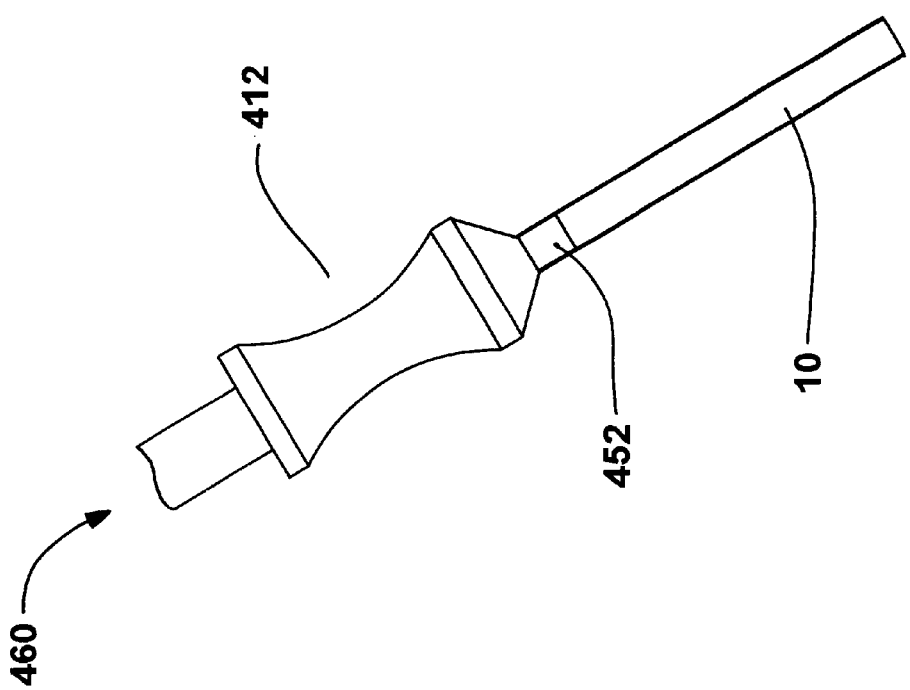
FIG. 7b is an enlarged schematic view of the stent holder of the invention holding a stent.
Figure 7A:
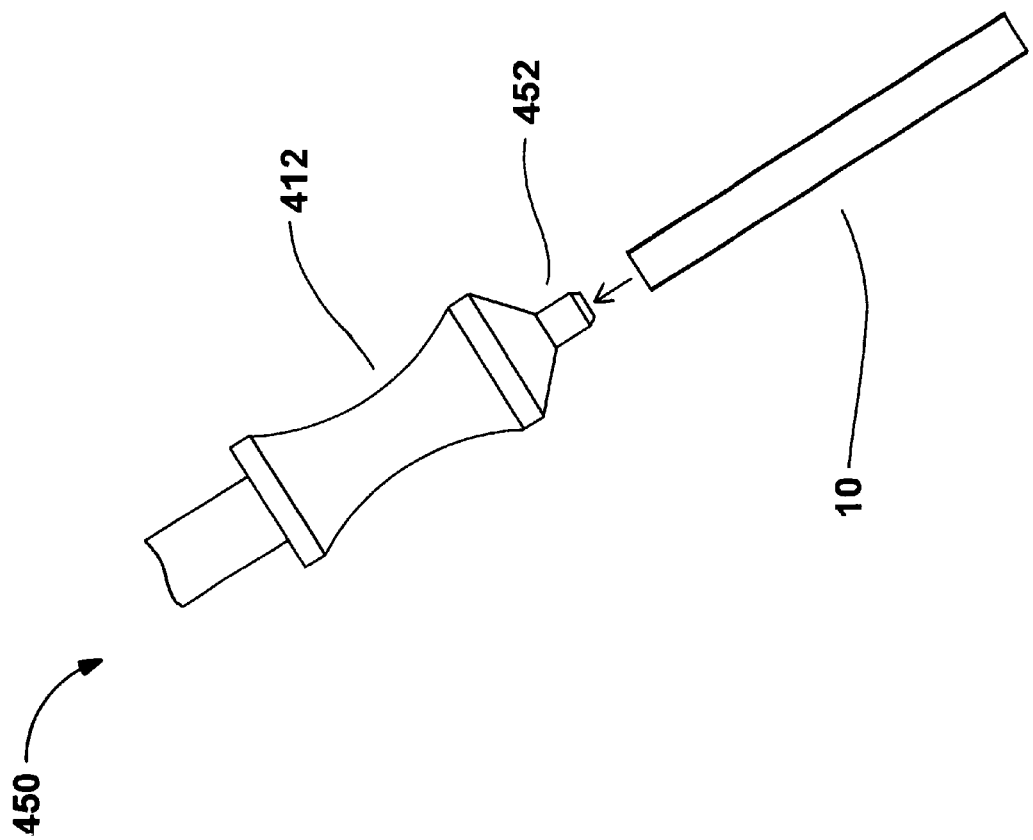
FIG. 7a is an enlarged schematic view of the stent holder of the invention and a schematic representation of a stent.

FIGS. 7a and 7b illustrate the method of attachment of a cylindrical medical coronary stent 10 to workpiece holder 412. Referring to FIG. 7a, which is a view 450 of a portion of workpiece holder 412 and stent 10 prior to attachment of the stent to the holder. Workpiece holder 412 has a cylindrical or slightly tapered end extension 452 for engaging the inner diameter of an end of the stent 10. Extension 452, or if tapered a portion of extension 452, has an outside diameter slightly (a few thousandths of an inch) greater than the inside diameter of the stent 10. An end of the stent 10 is inserted over the extension 452, causing the end of the stent 10 to expand slightly and to grip the extension 452 elastically, retaining the stent 10 on the extension 4522 of the workpiece holder 412 as shown in FIG. 7b. A stent 10 thus supported on the workpiece holder 412 of manipulator 400 in GCIB processing system is manipulated so as to assure smoothing of both interior and exterior surfaces of the stent 10 by the GCIB 302. A small portion of the inside diameter of stent 10 engages the workpiece holder extension 452 and does not receive GCIB processing. If it is desired that this engaged portion should receive GCIB processing, a second operation may be performed, repeating smoothing after reversing the stent 10 and mounting the previously smoothed end of the stent 10 on the holder extension 452, then repeating GCIB processing to smooth the portion not originally smoothed due to its engagement with holder extension 453. Depending on the material of the stent, the gas used to form cluster ions, and the degree of smoothing required, mean GCIB doses of from about $1\times10^{15}$ to about $1\times10^{17}$ ions/cm$^2$ provide useful smoothing of the medical coronary stents. I to $3\times10^{16}$ ionS/CM$^2$ is a preferred range of processing doses for 2 to 30 keV beams of argon, nitrogen, or oxygen GCIB's processing metal coronary stents according to the present invention.

Figure 8:
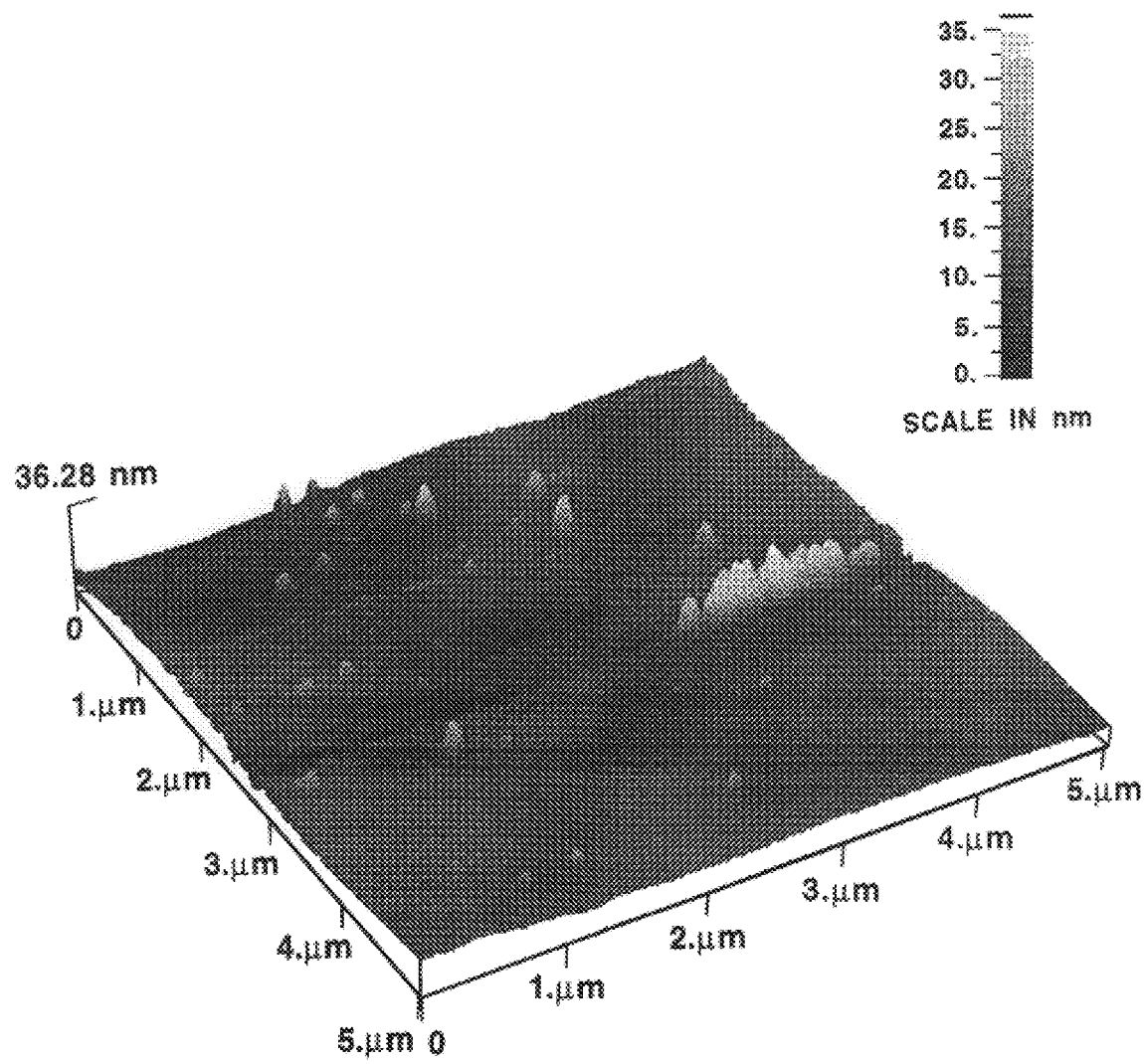
FIG. 8 is an atomic force microscope image showing the surface of medical coronary stent before GCIB processing.
Figure 9:
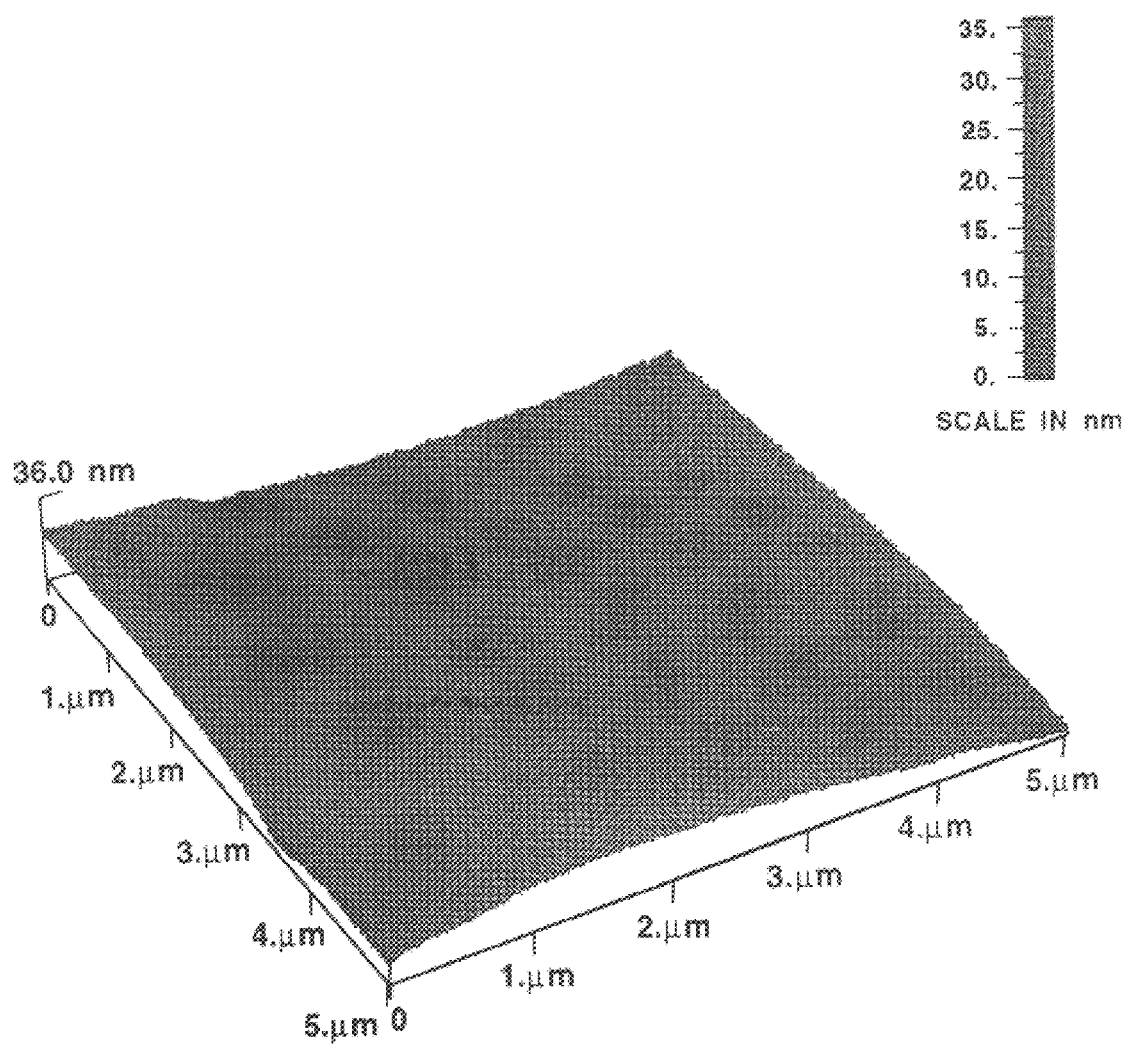
FIG. 9 is an atomic force microscope image showing the surface of a medical coronary stent after argon GCIB processing.

As the atomic force microscope (AFM) images shown in FIGS. 8 and 9 illustrate, it is possible to dramatically improve the surface smoothness on stents utilizing the present invention. FIG. 8 shows a stent before GCIB treatment with gross surface micro-roughness on a strut edge. The surface roughness measured an average roughness ($R_a$) of 113 angstroms and a root-mean-square roughness ($R_{RMS}$) of 148 angstroms. These irregularities highlight the surface micro-roughness problem at the cellular level where thrombosis begins. FIG. 9 shows a stent after GCIB processing where the surface micro-roughness has been eliminated without any measurable physical or structural change to the integrity of the stent itself. The post-GCIB-processed surface roughness measured an $R_a$ of 19 angstroms and an $R_{RMS}$ of 25 angstroms.

Figure 10:
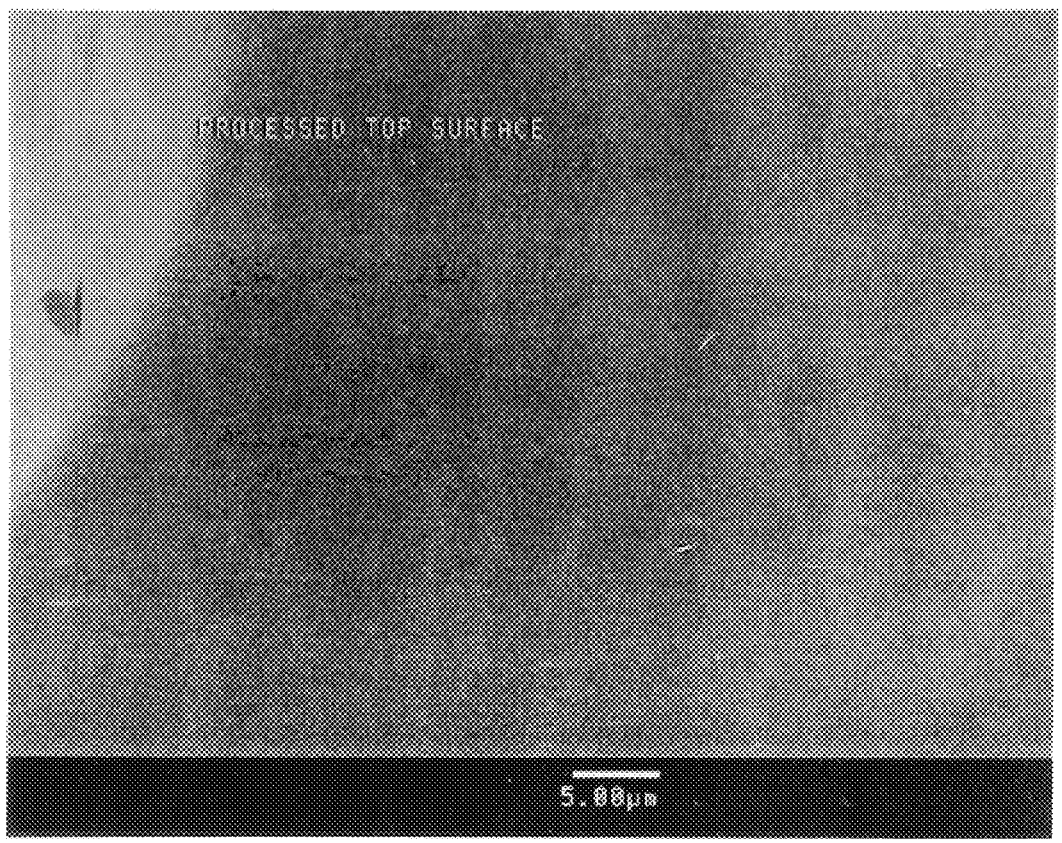
FIG. 10 is a high magnification scanning electron microscope image of a surface of a medical coronary stent following GCIB processing according to the present invention.

FIG. 10 is a high magnification scanning electron microscope image of a portion of an exterior surface of a stent of the type shown in FIGS. 1 and 2, but after GCIB processing according to the present invention. The quality of the surface has been greatly improved, as can be readily appreciated by comparing FIG. 10 with FIG. 2. FIG. 10 shows an exterior surface, but similar smoothing and cleaning is also typically observed on all surfaces of GCIB processed coronary stents.

Although the invention has been described with respect to various embodiments, it should be realized this invention is also capable of a wide variety of further and other embodiments within the spirit and scope of the appended claims.

What is claimed is:

1. An apparatus for smoothing and/or cleaning at least one surface of a medical stent comprising:
    a vacuum vessel;
    a gas cluster ion beam source within the vacuum vessel for producing a gas cluster ion beam;
    an accelerator for accelerating the gas cluster ion beam along a path having a beam axis; and
    a manipulator including a medical stent bolder for positioning the medical stent within the gas cluster ion beam path for processing.

2. The apparatus of claim 1, wherein the manipulator further comprises a repositioning mechanism for repositioning the medical stent such that the medical stent remains held within the gas cluster ion beam path.

3. The apparatus of claim 2, wherein the repositioning mechanism repositions the medical stent by rotating the medical stent about at least one axis.

4. The apparatus of claim 2, wherein the repositioning mechanism repositions the medical stent by rotating the medical stent about at least two different axes of rotation.

5. The apparatus of claim 4, wherein said at least two different axes of rotation intersect each other within the gas cluster ion beam path.

6. The apparatus of claim 4, wherein
    said at least two different axes of rotation and said beam axis all intersect each other at a common point;
    and said medical stent holder positions the medical stent at a predetermined angle with respect to at least one of said two different axes of rotation.

7. The apparatus of claim 6, wherein one of said at least two different axes of rotation intersects said beam axis approximately perpendicularly thereto.

8. The apparatus of claim 6, wherein said predetermined angle is in the range of approximately 15 degrees to approximately 45 degrees.

9. The apparatus of claim 6, wherein said predetermined angle is approximately 45 degrees.

10. The apparatus of claim 7, wherein said predetermined angle is in the range of approximately 15 degrees to approximately 45 degrees with respect to said one of said at least two different axes of rotation.

11. The apparatus of claim 7, wherein said predetermined angle is approximately 45 degrees with respect to said one of said at least two different axes of rotation.

12. The apparatus of claim 4, wherein the repositioning mechanism rotates the medical stent about two of said at least two different axes of rotation at two different rates of rotation.

13. The apparatus of claim 12, wherein the two different rates of rotation are in the ratio N:M, where N divided by M is not an integer and where M divided by N is not an integer.

14. The apparatus of claim 12, wherein the medical stent is substantially cylindrical and has an axis aligned with one of the two of said at least two different axes of rotation; and
rotation of the medical stent about said one of the two of said at least two different axes of rotation aligned with the stent axis is more rapid than rotation about the other of the two of said at least two different axes of rotation.

15. The apparatus of claim 2, wherein the repositioning mechanism positions multiple surfaces of the medical stent for irradiation by the gas cluster ion beam path at angles of beam incidence that are in the range of less than about +/−65 degrees from normal incidence of the beam axis with respect to the multiple surfaces of the medical stent.

16. The apparatus of claim 15, wherein the angles of beam incidence are in the range of less than about +/−45 degrees from normal incidence.

17. The apparatus of claim 1 further comprising scanning means for scanning the gas cluster ion beam and the medical stent relative to each other.

18. A method for smoothing and/or cleaning at least one surface of a medical stent comprising the steps of:
forming a gas cluster ion beam in a vacuum chamber;
accelerating the gas cluster ion beam;
positioning the medical stent in the vacuum chamber to receive the gas cluster ion beam for processing; and
irradiating at least one surface of the medical stent with a predetermined dose of gas cluster ions having a predetermined energy to reduce small scale surface roughness on the surface.

19. The method of claim 18, further comprising the step of rotating or repositioning the medical stent to process additional regions of the medical stent.

20. The method of claim 18, further comprising the step of rotating or repositioning the medical stent to irradiate two or more surface regions of the medical stent with a gas cluster ion beam.

21. The method of claim 20, wherein the gas cluster ion beam axis is incident on each irradiated surface region of the medical stent at an angle that is less than about +/−65 degrees from normal incidence with respect to said irradiated surface region of the medical stent for at least a portion of the time of irradiation of each irradiated surface region.

22. The method of claim 18, wherein the medical stent comprises an expandable metal coronary stent.

23. The method of claim 18, wherein the gas cluster ion beam comprises accelerated clusters of argon or oxygen or nitrogen.

24. An apparatus for holding and manipulating a cylindrical object having an object axis within a beam path having a beam axis, for surface irradiation, said apparatus comprising:
an object holder for positioning the cylindrical object in the path of the beam;
a repositioning mechanism operably connected to said object holder for repositioning the cylindrical object in the beam path by rotating the cylindrical object about at least a first axis of rotation and a second axis of rotation;
the first axis of rotation and the second axis of rotation intersecting each other within the beam path at an angle of intersection that is in the range of approximately 15 degrees to approximately 45 degrees; and
the cylindrical object being positioned by said object holder such that the object axis is substantially aligned with the second axis of rotation.

25. The apparatus of claim 24, wherein said first axis of rotation is substantially perpendicular to the beam axis.

26. An apparatus for modifying at least one surface of a medical stent comprising:
a vacuum vessel;
a gas cluster ion beam source within the vacuum vessel for producing a gas cluster ion beam;
an accelerator for accelerating the gas cluster ion beam along a path having a beam axis; and
a manipulator including a medical stent holder for positioning the medical stent within the gas cluster ion beam path for processing, said manipulator further comprising a repositioning mechanism for repositioning the medical stent in the gas cluster ion beam path by rotating said medical stent about at least two different axes of rotation at two different rates of rotation wherein said rates are in the ratio N:M, where N divided by M is not an integer and where M divided by N is not an integer.

27. An apparatus for modifying at least one surface of a medical stent comprising:
a vacuum vessel;
a gas cluster ion beam source within the vacuum vessel for producing a gas cluster ion beam;
an accelerator for accelerating the gas cluster ion beam along a path having a beam axis;
a manipulator including a medical stent holder for positioning the medical stent within the gas cluster ion beam path for processing; and
a scanning means for scanning the gas cluster ion beam and the medical stent relative to each other.

28. An apparatus for holding and manipulating a cylindrical object having an object axis within a beam path having a beam axis, for surface irradiation, said apparatus comprising:
an object holder for positioning the cylindrical object in the path of the beam;
a repositioning mechanism operably connected to said object holder for repositioning the cylindrical object in the beam path by rotating the cylindrical object about at least a first axis of rotation and a second axis of rotation;
the first axis of rotation and the second axis of rotation intersecting each other within the beam path at an angle of intersection that is in the range of approximately 15 degrees to approximately 45 degrees;
the cylindrical object being positioned by said object holder such that the object axis is substantially aligned with the second axis of rotation; and
a means for rotating said repositioning mechanism and said object holder such that the rotation of the cylindrical object about the first axis of rotation and about the second axis of rotation are at two different rates of rotation in the ratio N:M where N divided by M is not an integer and where M divided by N is not an integer.

29. The apparatus of claim 28, wherein the rate of rotation about the second axis of rotation is more rapid than the rate of rotation about the first axis of rotation.

30. An apparatus for holding and manipulating a cylindrical object having an object axis within a beam path having a beam axis, for surface irradiation, said apparatus comprising:

an object holder for positioning the cylindrical object in the path of the beam;

a repositioning mechanism operably connected to said object holder for repositioning the cylindrical object in the beam path by rotating the cylindrical object about at least a first axis of rotation and a second axis of rotation, wherein said first axis of rotation is substantially perpendicular to the beam axis;

the first axis of rotation and the second axis of rotation intersecting each other within the beam path at an angle of intersection that is in the range of approximately 15 degrees to approximately 45 degrees;

the cylindrical object being positioned by said object holder such that the object axis is substantially aligned wit the second axis of rotation; and a means for rotating said repositioning mechanism and said object holder such that the rotation of the cylindrical object about the first axis of rotation and about the second axis of rotation are at two different rates of rotation in the ratio N:M where N divided by M is not an integer and where M divided by N is not an integer.

31. The apparatus of claim 30, wherein the rate of rotation about the second axis of rotation is more rapid than the rate of rotation about the first axis of rotation.

32. An apparatus for holding and manipulating a cylindrical object having an object axis within a beam path having a beam axis, for surface irradiation, said apparatus comprising:

an object holder for positioning the cylindrical object in the path of the beam;

a repositioning mechanism operably connected to said object holder for repositioning the cylindrical object in the beam path by rotating the cylindrical object about at least a first axis of rotation and a second axis of rotation;

the first axis of rotation and the second axis of rotation intersecting each other within the beam path at an angle of intersection that is in the range of approximately 15 degrees to approximately 45 degrees; and the cylindrical object being positioned by said object holder such that the object axis is substantially aligned with the second axis of rotation, said object holder comprising a means for removably attaching to the cylindrical object by being inserted with the object along the object axis.

33. An apparatus for smoothing and/or cleaning at least one surface of a medical stent, the apparatus comprising:

a vacuum vessel;

a gas cluster ion beam source within the vacuum vessel for producing a gas cluster ion beam;

an accelerator for accelerating the gas cluster ion beam along a path having a beam axis;

a scanning means for scanning the gas cluster ion beam and the medical stent relative to each other; and a manipulator including a medical stent holder for positioning the medical stent for scanning by the gas cluster ion beam for processing said manipulator also repositioning the medical stent by rotating the medical stent about two different axes of rotation, said two different axes of rotation substantially intersecting each other at a point within the gas cluster ion beam path.

* * * * *

EX PARTE REEXAMINATION CERTIFICATE (5971st)
United States Patent
Kirkpatrick et al.

(10) Number: US 6,676,989 C1
(45) Certificate Issued: Oct. 23, 2007

(54) METHOD AND SYSTEM FOR IMPROVING THE EFFECTIVENESS OF MEDICAL STENTS BY THE APPLICATION OF GAS CLUSTER ION BEAM TECHNOLOGY

(75) Inventors: Allen R. Kirkpatrick, Lexington, MA (US); Robert K. Becker, Danvers, MA (US); Avrum Freytsis, Salem, MA (US)

(73) Assignee: Epion Corporation, Billerica, MA (US)

Reexamination Request:
No. 90/008,087, Jun. 28, 2006

Reexamination Certificate for:
Patent No.: 6,676,989
Issued: Jan. 13, 2004
Appl. No.: 09/901,204
Filed: Jul. 9, 2001

Related U.S. Application Data
(60) Provisional application No. 60/217,045, filed on Jul. 10, 2000.

(51) Int. Cl.
*C23F 3/00* (2006.01)

(52) U.S. Cl. .............. 427/2.28; 427/2.24; 427/595; 204/192.34; 204/298.27; 204/298.28; 204/298.36; 118/723 CB

(58) Field of Classification Search .............. None
See application file for complete search history.

(56) References Cited

U.S. PATENT DOCUMENTS 5,814,194 A * 9/1998 Deguchi et al. .......... 204/192.1
6,486,478 B1 * 11/2002 Libby et al. .............. 250/492.1

FOREIGN PATENT DOCUMENTS

JP        10066721        * 3/1998

OTHER PUBLICATIONS

Translation of JP-1066721.*

* cited by examiner

*Primary Examiner*—Kiley Stoner

(57) ABSTRACT

Numerous studies suggest that the current popular designs of coronary stents are functionally equivalent and suffer a 16 to 22 percent rate of restenosis. Although the use of coronary stents is growing, the benefits of their use remain controversial in certain clinical situations or indications due to their potential complications. The application of gas cluster ion beam (GCIB) surface modification such as smoothing or cleaning appears to reduce these complications and lead to genuine cost savings and an improvement in patient quality of life. The present invention is directed to the use of GCIB surface modification to overcome prior problems of thrombosis and restenosis. The atomic level surface smoothing of stents utilizing GCIB substantially reduces undesirable surface micro-roughness in medical coronary stents.

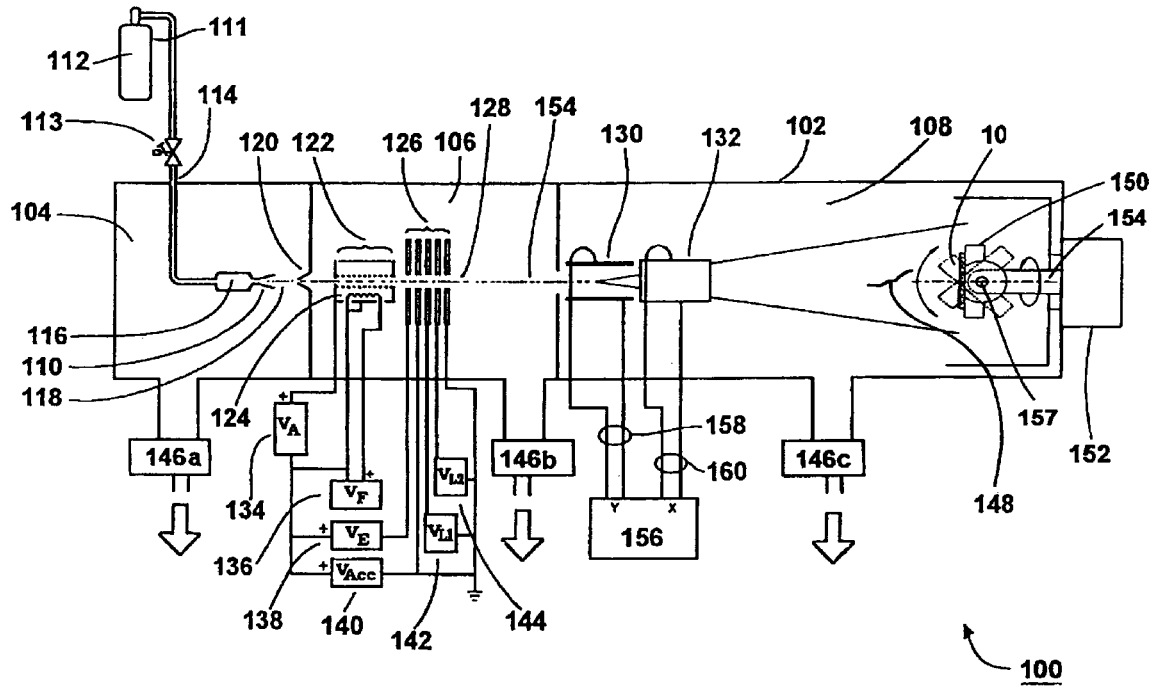

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 24–26 and 28–32 is confirmed.

Claim 2 is cancelled.

Claims 1, 3–4, 15, 18–20, 27 and 33 are determined to be patentable as amended.

Claims 5–14, 16–17 and 21–23, dependent on an amended claim, are determined to be patentable.

1. An apparatus for smoothing and/or cleaning at least one surface of a medical stent comprising:
   a vacuum vessel;
   a gas cluster ion beam source within the vacuum vessel for producing a gas cluster ion beam;
   an accelerator for accelerating the gas cluster ion beam along a path having a beam axis; and
   a manipulator including a medical stent [bolder] *holder* for positioning the medical stent within the gas cluster ion beam path for processing *and a repositioning mechanism adapted for repositioning the medical stent during processing such that the medical stent remains held within the gas cluster ion beam path.*

3. The apparatus of claim [2] *1*, wherein the repositioning mechanism [repositions the medical stent by rotating] *is adapted to rotate* the medical stent about at least one axis *passing either through the medical stent or through the gas cluster ion beam path*.

4. [The apparatus of claim 2] *An apparatus for smoothing and/or cleaning at least one surface of a medical stent comprising:*
   *a vacuum vessel;*
   *a gas cluster ion beam source within the vacuum vessel for producing a gas cluster ion beam;*
   *an accelerator for accelerating the gas cluster ion beam along a path having a beam axis; and*
   *a manipulator including a medical stent holder adapted for positioning the medical stent within the gas cluster ion beam path for processing and a repositioning mechanism adapted for repositioning the medical stent such that the medical stent remains held within the gas cluster ion beam path,* wherein the repositioning mechanism repositions the medical stent by rotating the medical stent about at least two different axes of rotation.

15. The apparatus of claim [2] *1*, wherein the repositioning mechanism positions multiple surfaces of the medical stent for irradiation by the gas cluster ion beam path at angles of beam incidence that are in the range of less than about +/−65 degrees from normal incidence of the beam axis with respect to the multiple surfaces of the medical stent.

18. A method for smoothing and/or cleaning at least one surface of a medical stent comprising the steps of:
   forming a gas cluster ion beam in a vacuum chamber;
   accelerating the gas cluster ion beam;
   positioning the medical stent in the vacuum chamber to receive the gas cluster ion beam for processing; and
   irradiating [at least one surface of] the medical stent with a predetermined dose of gas cluster ions having a predetermined energy to reduce small scale surface roughness on the surface; *and*
   *repositioning the medical stent during the step of irradiating to process additional regions of the medical stent.*

19. The method of claim 18, [further comprising] *wherein* the step of [rotating or] repositioning the medical stent to process additional regions of the medical stent *includes rotating the medical stent around an axis passing through the medical stent*.

20. The method of claim 18, [further comprising] *wherein* the step of [rotating or] repositioning the medical stent [to irradiate two or more surface regions of the medical stent with a gas cluster ion beam] *includes rotating the medical stent around an axis passing through an axis of the gas cluster ion beam*.

27. An apparatus for modifying at least one surface of a medical stent comprising:
   a vacuum vessel;
   a gas cluster ion beam source within the vacuum vessel for producing a gas cluster ion beam;
   an accelerator for accelerating the gas cluster ion beam along a path having a beam axis;
   a manipulator including a medical stent holder for positioning the medical stent within the gas cluster ion beam path for processing *and being adapted for rotating or repositioning the medical stent during processing such that the medical stent remains held within the gas cluster ion beam path*; and
   a scanning means for scanning the gas cluster ion beam and the medical stent relative to each other.

33. An apparatus for smoothing and/or cleaning at least one surface of a medical stent, the apparatus comprising:
   a vacuum vessel;
   a gas cluster ion beam source within the vacuum vessel for producing a gas cluster ion beam;
   an accelerator for accelerating the gas cluster ion beam along a path having a beam axis;
   a scanning means for scanning the gas [duster] *cluster* ion beam and the medical stent relative to each other; and
   a manipulator including a medical stent holder for positioning the medical stent for scanning by the gas cluster ion beam for processing said manipulator also repositioning the medical stent by rotating the medical stent about two different axes of rotation, said two different axes of rotation substantially intersecting each other at a point within the gas cluster ion beam path.

* * * * *